(12) United States Patent
Mitchell et al.

(10) Patent No.: US 10,324,031 B2
(45) Date of Patent: Jun. 18, 2019

(54) HIGH INDEX-CONTRAST PHOTONIC DEVICES AND APPLICATIONS THEREOF

(71) Applicant: Royal Melbourne Institute of Technology, Melbourne (AU)

(72) Inventors: Arnan Mitchell, Alphington (AU); Thach G. Nguyen, Vermont (AU); Kiplimo Yego, Caulfield North (AU); Anthony Hope, Mount Evelyn (AU)

(73) Assignee: Royal Melbourne Institute of Technology, Melbourne (AU)

( * ) Notice: Subject to any disclaimer, the term of this patent is extended or adjusted under 35 U.S.C. 154(b) by 0 days.

(21) Appl. No.: 15/560,434

(22) PCT Filed: Mar. 22, 2016

(86) PCT No.: PCT/AU2016/050201
§ 371 (c)(1),
(2) Date: Sep. 21, 2017

(87) PCT Pub. No.: WO2016/149749
PCT Pub. Date: Sep. 29, 2016

(65) Prior Publication Data
US 2018/0067255 A1    Mar. 8, 2018

(30) Foreign Application Priority Data

Mar. 23, 2015 (AU) ................................ 2015901035

(51) Int. Cl.
*G02B 1/00* (2006.01)
*G02B 5/30* (2006.01)
(Continued)

(52) U.S. Cl.
CPC ............. *G01N 21/45* (2013.01); *G02B 1/005* (2013.01); *G02B 5/30* (2013.01); *G02B 6/293* (2013.01);
(Continued)

(58) Field of Classification Search
CPC .................... G02B 6/02295; G02B 6/105; G02B 6/03677; G02B 6/12033; G02B 6/136;
(Continued)

(56) References Cited

U.S. PATENT DOCUMENTS

2006/0228074 A1    10/2006   Lipson et al.
2012/0008897 A1    1/2012    Li
2015/0001175 A1*   1/2015    Rabiei .................... B82Y 20/00
                                                          216/24

FOREIGN PATENT DOCUMENTS

WO    2008-082664 A2    7/2008

OTHER PUBLICATIONS

International Search Report issued in corresponding application No. PCT/AU2016/050201 dated Jun. 21, 2016 (2 pages).
(Continued)

*Primary Examiner* — Michael P Mooney
(74) *Attorney, Agent, or Firm* — Osha Liang LLP

(57) ABSTRACT

A photonic processing module (100) comprises a high index-contrast waveguide device comprising a substrate (102), a first layer (104) disposed on the substrate having a first refractive index, and a relatively thin second layer (106) disposed on the first layer. The second layer has a second refractive index providing a high index-contrast with the first layer, and the device includes at least one thin-ridge waveguide element (108) formed in the second layer which supports a guided mode in a longitudinal direction. An optical input port (110) is configured to direct an input beam into a slab mode of the second layer, the beam being directed to propagate at a predetermined angle θ to the longitudinal direction of the thin-ridge waveguide element. The angle θ is associated with a resonant coupling between the slab mode of the second layer and the guided mode of the thin-ridge waveguide element. An output beam is thus generated when the input beam includes one or more optical
(Continued)

components corresponding with the resonant coupling. An optical output port (112) is configured to receive the output beam.

26 Claims, 14 Drawing Sheets

(51) Int. Cl.
*G02F 1/01* (2006.01)
*G01N 21/45* (2006.01)
*G02B 6/293* (2006.01)
*G02F 1/025* (2006.01)
*G02F 1/313* (2006.01)

(52) U.S. Cl.
CPC ............... *G02F 1/01* (2013.01); *G02F 1/025* (2013.01); *G02F 1/3138* (2013.01); *G02F 2201/063* (2013.01); *G02F 2201/30* (2013.01); *G02F 2202/105* (2013.01); *G02F 2203/05* (2013.01)

(58) Field of Classification Search
CPC .......... G02B 6/14; G02B 6/1223; G02B 5/30; G02F 1/3558; G02F 1/225; G02F 1/035; G01N 21/45
USPC ................. 385/1–14, 27, 28, 38, 39, 43, 46, 385/129–132
See application file for complete search history.

(56) References Cited

OTHER PUBLICATIONS

Written Opinion of the International Searching Authority issued in corresponding application No. PCT/AU2016/050201 dated Jun. 21, 2016 (14 pages).

Nguyen et al., "Rigorous Modeling of Lateral Leakage Loss in SOI Thin-Ridge Waveguides and Couplers"; IEEE Photonics Technology Letters, vol. 21, No. 7, pp. 486-488; Apr. 1, 2009 (3 pages).

* cited by examiner

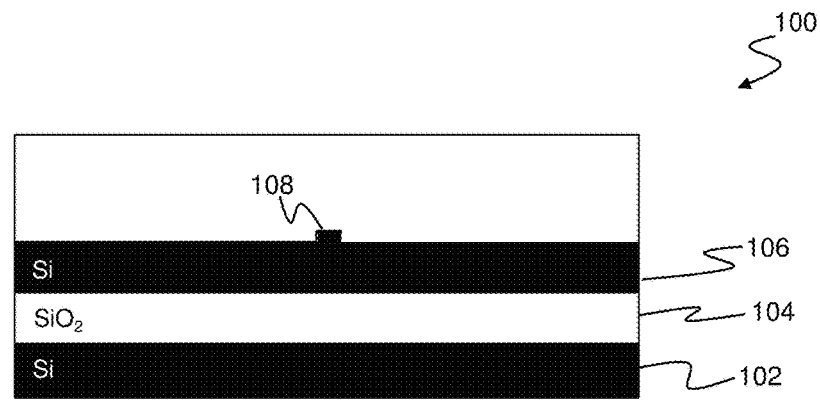
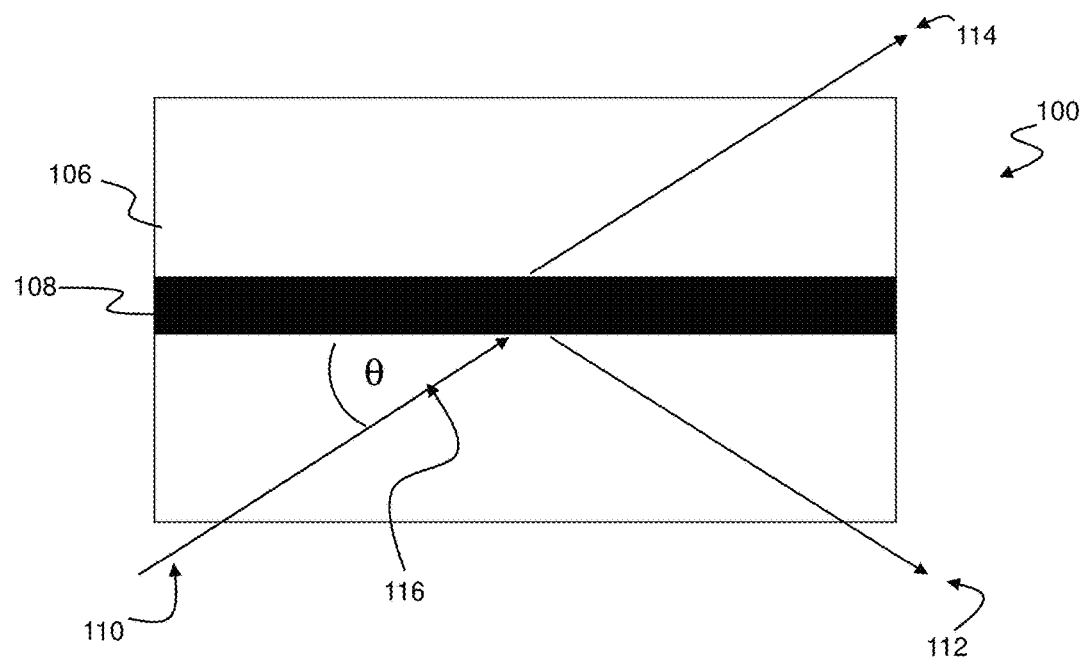
Figure 1(a)
Figure 1(b)

HIGH INDEX-CONTRAST PHOTONIC DEVICES AND APPLICATIONS THEREOF

FIELD OF THE INVENTION

The present invention relates to photonic circuits, and more particularly to silicon-on-insulator (SOI) and other high index-contrast photonic devices including resonant structures, along with applications of such devices and structures.

BACKGROUND OF THE INVENTION

Silicon-based technologies have long been the dominant driver of modern microelectronics. In the decades since the first rudimentary silicon electronic devices were demonstrated, continuing advances have resulted in ever smaller, faster, and more highly integrated components and circuits.

More recently, photonic technology, in which information is carried via optical rather than electronic signals, has matured as a technology for transmission of information, particularly in the form of long-haul optical fibre communications systems. A basic photonic system includes a light source (e.g. a laser), a modulator for impressing information upon an optical signal, a waveguide, and a photodetector. However, in contrast to silicon electronics, where all components can be integrated onto a single chip, current generation photonic systems are mainly based on discrete components and serial fabrication. There has long been a desire to transfer the benefits of mature silicon fabrication technology into the field of photonics, including the development of integrated circuits combining both photonic and electronic components. Optical transmission can achieve much higher data rates than metallic conductors, without creating problems associated with electromagnetic interference. Integrated photonic/electronic circuits could therefore provide new functionality, along with faster communication between circuit boards, chips on a board, and even between different elements on a single chip.

Silicon photonic technologies could also be useful to provide optical processing functions in optical communications systems, such as switching, filtering, and wavelength-based processing, such as multiplexing and demultiplexing of optical channels. Applications of photonic circuits may also be found in the field of sensing.

In addition to the availability of mature fabrication processes, silicon itself has a number of desirable physical properties. For example, silicon has a high thermal conductivity and a high optical damage threshold, and is therefore an advantageous choice of material for photonic applications. Silicon-on-insulator (SOI) wafers are available at relatively low cost, and high quality, providing the promise of efficient and cost-effective fabrication of CMOS-compatible planar lightwave circuits.

Similar considerations apply to other established technologies and materials, such as silicon nitride ($Si_3N_4$), semiconductor materials such as InP and other III-V semiconductors, and high-index glasses, such as chalcogenide and tellurite glasses.

A key element in a wide range of optical circuit applications is a resonator. Resonators can be used in a range of applications, such as wavelength filtering, dispersion engineering, and field enhancement.

There is, accordingly, a continuing demand for the development of new resonant structures that can be efficiently fabricated in SOI technology, which are compact, and which can be employed in a range of optical and opto-electronic signal processing, communications, sensing, and other applications. Embodiments of the present invention provide a range of novel devices that address these requirements.

SUMMARY OF THE INVENTION

In one aspect, the present invention provides a photonic processing module comprising:

a high index-contrast waveguide device comprising a substrate, a first layer disposed on the substrate having a first refractive index, and a relatively thin second layer disposed on the first layer which has a second refractive index providing a high index-contrast with the first layer, the device including at least one thin-ridge waveguide element formed in the second layer which supports a guided mode in a longitudinal direction;

an optical input port configured to direct an input beam into a slab mode of the second layer, the beam being directed to propagate at a predetermined angle $\theta$ to the longitudinal direction of the thin-ridge waveguide element, wherein the predetermined angle $\theta$ is associated with a resonant coupling between the slab mode of the second layer and the guided mode of the thin-ridge waveguide element, whereby an output beam is generated when the input beam comprises one or more optical components corresponding with the resonant coupling; and a first optical output port configured to receive the output beam.

In practical embodiments, an index contrast of, e.g., 15%-20% or greater between the second refractive index and the first refractive index is suitable to achieve the benefits of the invention. In the embodiments described herein, the waveguide device is a silicon-on-insulator (SOI) device, wherein the first layer is an insulating layer, such as silicon dioxide ($SiO_2$) while the second layer is a silicon layer (SOI layer). However, in alternative embodiments a high index-contrast waveguide may be formed from other suitable materials, such as silicon nitride ($Si_3N_4$), semiconductor materials such as InP and other III-V semiconductors, and high-index glasses, such as chalcogenide and tellurite glasses.

Photonic processing modules embodying the invention exploit a surprising property of high index-contrast thin-ridge waveguides that has been discovered by the inventors. In particular, when a transverse electric (TE) optical beam is incident on a thin-ridge waveguide element which supports a strongly guided transverse magnetic (TM) mode there is an angle of incidence at which the TE slab mode is phase-matched with the TM guided mode. Energy therefore couples from the TE slab mode to the TM guided mode, but surprisingly this energy is coupled back into a reflected TE beam. The reflection coefficient of the TE beam is found to depend upon parameters including incident angle, wavelength and waveguide structure/geometry. The interaction is strongly resonant.

It should be noted that where reference is made in the present specification to optical 'ports', or more particularly 'input ports' or 'output ports', these terms should be interpreted broadly to encompass any well-defined volume or region of space through which optical beams pass by virtue of the configuration of the associated processing module embodying the invention. Optical ports may comprise waveguide structures, collimating lenses, and/or other physical components defining a particular input or output path for optical beams. However, optical ports may also comprise slab regions of an SOI (or other high index-contrast) device, or regions of free space, through which optical beams pass when propagating between processing modules and/or other components of a photonic circuit or system. Furthermore, unless otherwise restricted by the particular construction of a module, circuit or device, the propagation of optical fields is generally reversible or bidirectional. Accordingly, the specific identification of 'input' and 'output' ports is provided to facilitate understanding, without intending any loss of generality regarding the actual direction of propagation of optical beams in particular applications of the device, module or system.

In some embodiments of the invention, the waveguide device includes a plurality of parallel, coupled, thin-ridge waveguide elements. The number, and associated dimensions, of the plurality of waveguide elements may be selected to achieve a desired characteristic spectral response of the SOI waveguide device. Through appropriate design and fabrication of thin-ridge waveguide elements, the characteristic spectral response may approximate a characteristic of a conventional RF filter design, such as a Butterworth filter response, a Chebyshev filter response, or an elliptic filter response.

In some embodiments, the waveguide device further comprises a plurality of dielectric loading elements disposed adjacent to, and spaced apart from, the waveguide elements, and the number, and associated dimensions, of the parallel, coupled, thin-ridge waveguide elements, and the number, associated dimensions, and spacings of the dielectric loading elements from the waveguide elements, are selected to achieve a desired characteristic spectral response of the high index-contrast waveguide device.

A photonic processing module embodying the invention may further comprise a second optical output port configured to receive a transmitted beam which comprises one or more components not corresponding with the resonant coupling. In such arrangements, for example, frequency components of an input beam that are 'on resonance' are reflected to the first output port, while 'off resonance' frequency components are transmitted to the second output port.

According to some embodiments of the invention, the SOI waveguide device further comprises refractive index modulating means adapted to enable a refractive index of at least a portion of the SOI layer to be perturbed. The refractive index modulating means may be a heating element. Alternatively, the refractive index modulating means may be a fluid, having a different refractive index from the thin-ridge waveguide element applied on top of the thin-ridge waveguide element. Liquid crystal structures may also be used as modulating means in some embodiments.

In still other embodiments, the refractive index modulating means is an electro-optic modulator configured to modify a free carrier concentration in the thin-ridge waveguide element in response to an electrical input signal. The electro-optic modulator may comprise a PIN diode, wherein the thin-ridge waveguide element is formed within the intrinsic (I) region of the PIN diode.

In further embodiments, the angle at which the optical input port is configured to direct the input beam may be made adaptable over a range, such as a range of 1.0 degree, 2.0 degrees, or similar order, whereby a characteristic wavelength of the resonant coupling is tunable.

Embodiments of the invention may be employed in a number of different applications, including:
wavelength-selective optical filters;
wavelength selective multiplexer/demultiplexer components;
tunable optical filters;
polarisation beam splitters;
sensors;
beam splitters
interferometers; and
dispersion engineering devices, including dispersion compensation devices.

Further details of the principles of operation of the invention, along with various applications and configurations, and their associated benefits and advantages, will be appreciated from the following disclosure of various embodiments. These embodiments are, however, provided by way of example, and are not intended to be limiting of the overall scope of the invention as defined in any of the preceding statements, or in the claims appended hereto.

BRIEF DESCRIPTION OF THE DRAWINGS

Embodiments of the invention will now be described with reference to the accompanying drawings, in which like reference numerals indicate like features, and wherein:

FIGS. 1($a$) and ($b$) are schematic diagrams showing a cross-section and top view of a silicon-based photonic processing module embodying the invention;

FIG. 9($b$) shows a schematic cross-section of a third-order thin-ridge waveguide reflector element according to another embodiment of the invention;

FIG. 11($b$) is a graph showing an exemplary reflection spectrum corresponding with a reflector including the embodiment illustrated in FIG. 9($b$);

FIG. 11($c$) is a graph showing a tuning effect of changing the angle of incidence of a light beam to the embodiment illustrated in FIG. 9($b$);

DETAILED DESCRIPTION OF EMBODIMENTS

Figure 2:
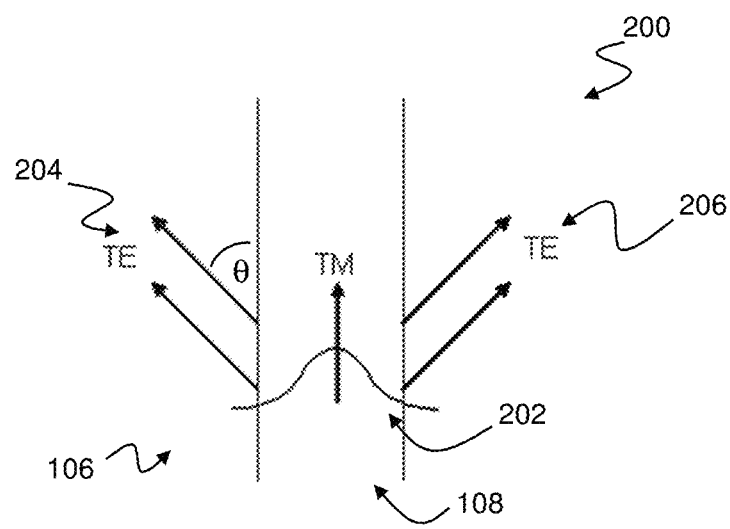
FIG. 2 is an illustration of lateral leakage from an SOI thin-ridge waveguide structure.

FIG. 1(a) shows a schematic cross-section of a silicon-based photonic processing module 100 embodying the invention, while FIG. 1(b) shows a corresponding schematic top view. The module includes a silicon-on-insulator (SOI) waveguide device which comprises a substrate 102, such as a silicon substrate. An insulating layer 104, such as a silicon dioxide layer, is disposed on the substrate 102. Finally, a relatively thin silicon layer 106 (SOI layer) is disposed on the insulating layer 104. A thin-ridge waveguide element 108 is formed in the SOI layer. The thin-ridge waveguide element 108 may be formed using conventional silicon processing steps, such as etching or electron-beam lithography.

The height of the silicon ridge 108 may be on the order of nanometers to tens of nanometers, for example on the order of 10 nm, or anywhere between about 10 nm and about 120 nm. The thin-ridge waveguide element 108 supports a transverse magnetic (TM) guided mode which propagates in a longitudinal direction, i.e. from left to right, or right to left, in FIG. 1(b).

In addition to the TM modes guided by the thin-ridge waveguide 108, the thin silicon film layer 106 also supports slab modes, which are oriented in the transverse electric (TE) polarisation, and which are confined vertically, but which radiate laterally outside the region of the ridge 108.

For thin-ridge waveguides, such as waveguide 108, the effective index of the guided TM mode is lower than that of the TE slab modes. Consequently, the guided TM mode may be longitudinally phase-matched to a radiating TE slab mode which is propagating at a significant angle to the guided TM mode. This is illustrated by the schematic diagram 200 shown in FIG. 2. The guided TM mode 202 propagates longitudinally along the waveguide 108. The indexed discontinuity at the shallow ridge walls causes power in the guided TM mode to couple to phase-matched TE slab modes. As a result, the guided TM mode continually loses power to TE slab modes, e.g. 204, 206, which propagate at an angle θ to the propagation direction of the guided TM mode. It can be shown that the angle θ is given by the expression:

$$\cos\theta = \frac{N_{eff}^{TM}}{N_{slab}^{TE}} \quad (1)$$

where $N_{eff}^{TM}$ is the effective index of the guided TM mode, and $N_{slab}^{TE}$ is the effective index of the radiating TE slab mode.

For typical thin-ridge waveguide dimensions, the propagating angle of the radiating TE slab modes is around 50 degrees.

This lateral leakage from simple straight thin-ridge SOI waveguides was experimentally observed and described by Webster et al, 'Width-dependence of inherent TM mode lateral leakage loss in silicon on insulator ridge waveguides,' IEEE Photonics Technology Letters, Volume 19, No. 6, pages 429-431, 15 Mar. 2007. An analysis of the phenomenon may be found in Nguyen et al, 'Rigorous modelling of lateral leakage loss in SOI thin-ridge waveguides and couplers,' IEEE Photonics Technology Letters, Volume 21, No. 7, pages 486-488, 1 Apr. 2009.

Embodiments and applications of the present invention are based upon a novel and unexpected discovery of the present inventors. While it may be expected that an incident TE beam applied via an input port 110 at an angle θ 116 to the thin-ridge waveguide 108 would result in a gradual coupling of power from the incident TE mode to the guided TM mode of the waveguide 108, the present inventors have identified a surprising resonant property. In particular, for an appropriately determined angle θ, and corresponding wavelength (or, equivalently, frequency) of the incident light beam, the incident beam is, in fact, reflected from the waveguide 108 in the direction of a correspondingly positioned output port 112. When these resonant conditions are not satisfied, the incident beam is transmitted via the slab mode to a correspondingly positioned second optical output port 114.

Figure 3:
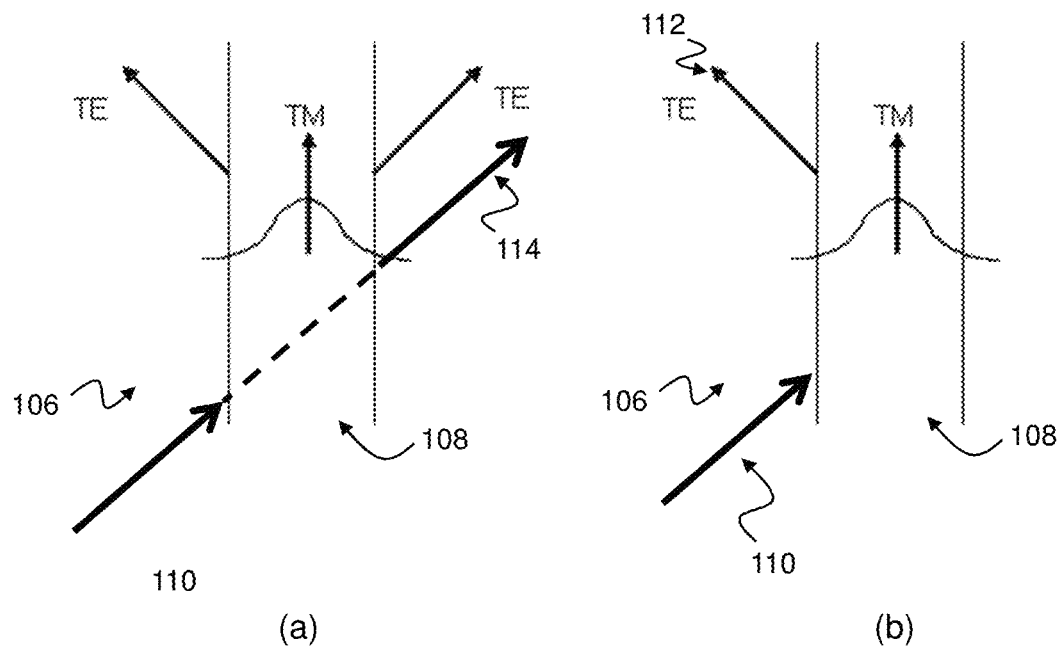
FIGS. 3($a$) and ($b$) are illustrations of transmission and reflection of incident beams according to embodiments of the invention.

These processes are further illustrated in FIG. 3, in which FIG. 3(a) shows schematically transmission of an incident beam, while FIG. 3(b) shows schematically reflection of an incident beam, according to embodiments of the invention. The phenomena illustrated in these diagrams may be explained as follows.

When a TE wave 110 is incident on the waveguide 108 from the left side (as represented in FIG. 3), at an angle θ equal to the TE radiation angle of the guided TM mode, a portion of the energy in the TE wave will couple to the guided mode. The remainder of the TE wave passes through the waveguide region to the right-hand side. At the same time, the TM mode guided within the waveguide 108 will generate leakage TE waves on both sides of the waveguide. The phase differences between the generated TE waves leaking from the guided TM mode, and the TE wave transmitted through the waveguide, are such that the TE waves on the right-hand side of the waveguide 108 will interfere destructively resulting in no TE field appearing on the right-hand side of the waveguide. Conversely, constructive interference occurs on the left-hand side of the waveguide 108, whereby a reflected beam 112 is generated. Thus the 'lateral leakage waveguide' 108 may be employed as a resonator for the TE slab wave 110.

Rigorous numerical modelling of structures embodying the invention has revealed highly unusual properties. Typically, a strong resonance requires a longer path length (such as in a ring resonator) or a very strong index contrast (such as the holes in photonic crystals). However, the novel resonator structure of the present invention achieves a very strong resonance despite being very compact (the width of the waveguide may be on the order of, or less than, 1 μm). This enables a high level of integration of modules embodying the invention, for example allowing multiple resonator structures to be assembled on a single chip into sophisticated superstructures.

Figure 4:
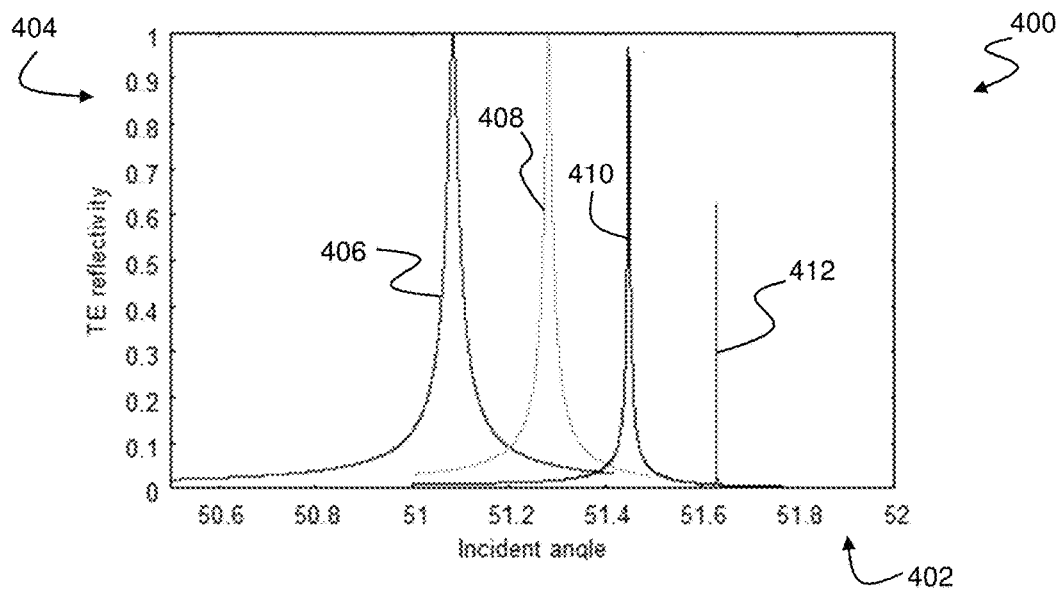
FIG. 4 is a graph showing TE reflectivity of embodiments of the invention as a function of incident angle.
Figure 5:
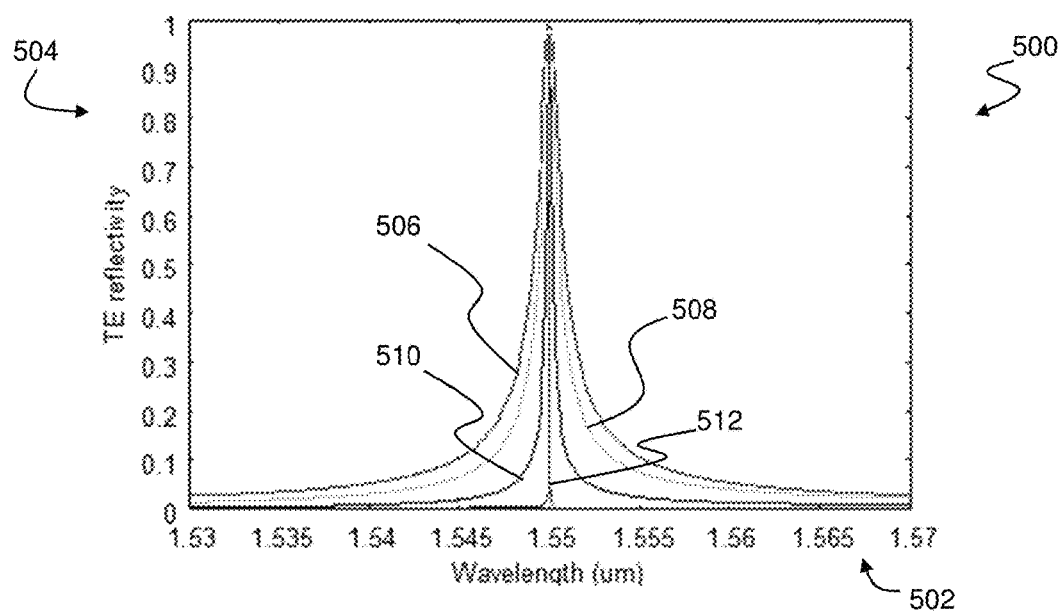
FIG. 5 is a graph showing TE reflectivity of embodiments of the invention as a function of wavelength.

By way of illustration, FIGS. 4 and 5 are graphs showing TE reflectivity as a function of incident angle and of wavelength respectively. The graph 400 shows incident angle on the horizontal axis 402, and the TE reflection coefficient on the vertical axis 404. Four curves on the graph 400 correspond with four different widths for the waveguide 108. These widths are 1.40 μm (406), 0.9 μm (408), 0.8 μm (410), and 0.7 μm (412). As can be seen, there is a small variation in the incident angle required for resonance, which depends upon the waveguide width. Furthermore, waveguides of a narrower width exhibit a sharper resonance.

The graph 500 in FIG. 5 shows wavelength along the horizontal axis 502 and the TE reflection coefficient on the vertical axis 504. Again, four different waveguide widths are illustrated, being 1.04 µm (506), 0.9 µm (508), 0.8 µm (510), and 0.7 µm (512).

FIGS. 4 and 5 clearly illustrate that a single waveguide can be employed within a module embodying the invention to provide a wavelength selective filter or resonator having a Q factor which is, in this case, defined by the width of the waveguide. In general, other parameters of the waveguide, such as the height and composition, also affect the Q factor.

According to further embodiments of the invention, the SOI waveguide device may comprise a plurality of coupled, thin-ridge waveguide elements. In the simplest arrangement, the waveguide elements are aligned in parallel, as illustrated schematically in the arrangement 600 shown in FIG. 6. In this arrangement, an array of waveguides 602 is provided, in which a number of physical parameters may be exploited in order to control the overall characteristic (e.g. reflectivity and transmitivity spectra) of the device 600. The controllable parameters may include width of each waveguide, spacing of waveguides, and height of each waveguide. Preferably, the effective index of the TM mode supported by all waveguides is the same, in order to maximise coupling between TE and TM modes across all waveguides, for the same angle θ. Accordingly, where waveguides having differing widths are employed, one mechanism to match the effective indices is to adjust waveguide height. In practice, however, fabricating devices with varying waveguide heights may be difficult using conventional and widely available silicon fabrication processes. Accordingly, other techniques for matching the effective indices may be employed, such as selective doping of waveguides in order to alter the material refractive index, application of additional layers on top of the waveguides, addition of dielectric loading elements, incorporation of dimples or other structures in the waveguide, and so forth.

Figure 6:
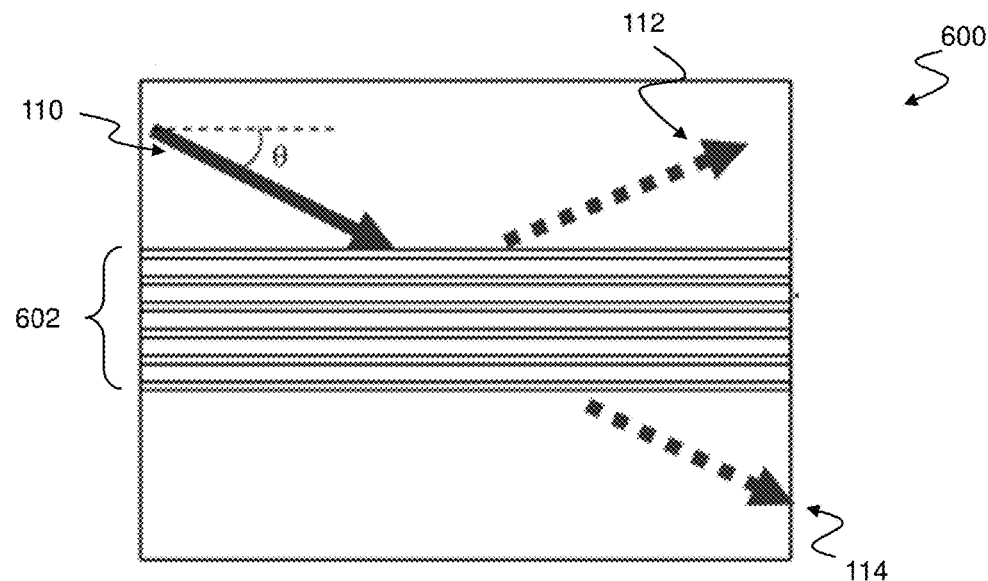
FIG. 6 is a schematic illustration of a silicon-based photonic processing module comprising a plurality of parallel, coupled, thin-ridge waveguide elements.
Figure 7:
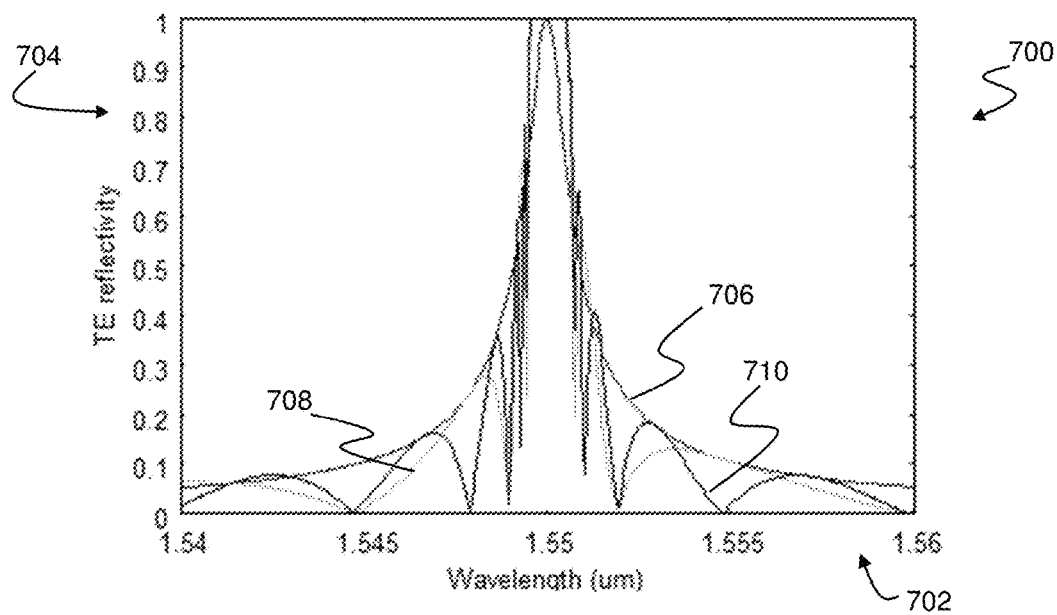
FIG. 7 is a graph showing spectral response of modules as shown in FIG. 6 for different numbers of waveguide elements.

FIG. 7 is a graph 700 showing spectral responses of modules employing parallel, coupled, thin-ridge waveguide elements as illustrated in FIG. 6. The horizontal axis 702 shows wavelength, while the vertical axis 704 is TE mode reflectivity between input beam 110 and output beam 112. Results are shown for three different structures, having one period 706, five periods 708, and 10 periods 710 respectively. Notably, increasing the number of thin-ridge waveguide elements results in a flattening of the pass band, while spectral ripples within the stop band remain bounded by the single waveguide response.

Similar properties are observed in coupled resonator array filters employed within the field of microwave engineering. Techniques for synthesising such filters are well-known, and similar techniques have been employed for the synthesis of coupled ring-resonator optical waveguides, e.g. by Yariv et al, 'Coupled Resonator Optical Waveguide: A proposal and analysis,' *Optics Letters*, Volume 24, page 711 (1999). In filter synthesis, it is preferable that the size of each resonator is smaller than the operating wavelength, which is easily achieved within the microwave domain, but less commonly practical within the optical domain. However, the results shown in the graph 500 of FIG. 5 indicate that, for example, filters operating at a wavelength of 1.55 µm can be fabricated in accordance with the principles of the present invention using thin-ridge waveguides having a width of 1 µm or less. Accordingly, modules embodying the present invention may be synthesised using techniques drawn from the field of microwave engineering.

Accordingly, for example, filters having spectral responses approximating common microwave filter types, such as Butterworth, Chebyshev, or elliptical filters, may be synthesised based upon the use of filter-design tables developed for use in the microwave field. The designer may therefore select a filter order, a desired pass- and/or stop-band ripple (depending on filter type), and then look up a corresponding filter design table in order to determine a required Q factor of each resonator. For a given slab thickness, the required effective index at the intended operating wavelength can be determined, in conjunction with the required incident angle (see Equation 1, and FIGS. 4 and 5). The parameters of each waveguide (e.g. width, height, or other controllable physical parameters) are then determined in order to provide the correct Q factor while achieving the required effective index value.

The utility of this design approach will now be demonstrated, with reference to FIGS. 8 to 13. FIGS. 8(a), (b) and (c) show examples of computed field intensity for a module employing a single waveguide resonator. The field intensity plot 800 corresponds with an input beam 802 having a 10 nm bandwidth, a wavelength of 1550 nm (corresponding with the waveguide resonance) and a Gaussian profile of 200 µm full-width half-maximum (FWHM). As shown, the majority of the energy in this on-resonance beam is reflected and propagates as output beam 804.

The computed field intensity 806 corresponds with a similar beam, but having a central frequency of 1555 nm, thus corresponding with a band edge of the waveguide resonator. The input beam 808 is partially reflected 810 and partially transmitted 812, i.e. the waveguide resonator acts as a beam splitter.

The computed field intensity 814 corresponds with an input beam 816 having a central wavelength of 1560 nm, which is therefore off-resonance with the waveguide. The majority of the light in this beam is transmitted 820, with only a small residual reflection 818.

Figure 9A:
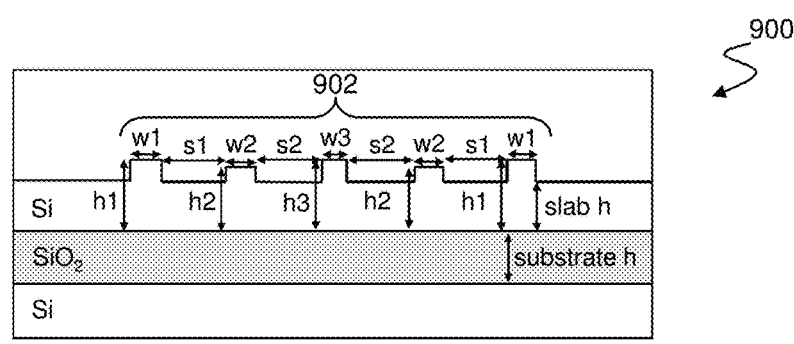
FIG. 9($a$) shows a schematic cross-section of a fifth-order thin-ridge waveguide reflector element embodying the invention.

FIG. 9(a) shows a schematic cross-section of a fifth-order thin-ridge waveguide reflector element embodying the invention. The spacing, width and height of the five waveguides 902 of the reflector element 900 may be determined in accordance with the synthesis methods described above. According to a first example, a fifth-order Butterworth filter has been designed, in which the dimensions have been determined as follows: w1=511.5 nm; h1=224.5 nm; s1=2.298 µm; w2=395 nm; h2=229.5 nm; s2=2.377 µm; w3=356.5 nm; h3=232 nm; slab thickness is 200 nm; and substrate thickness is 1.5 µm. It may be noted that the substrate thickness is not critical, however providing for at least 1.5 µm ensures that substrate leakage is not significant.

Figure 9B:
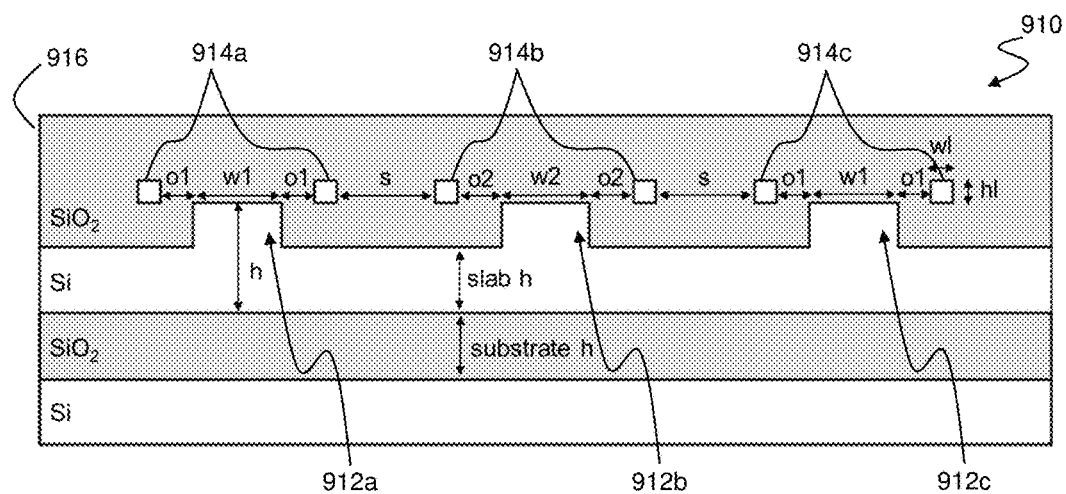

As has been mentioned, alternatives to varying the waveguide heights include the incorporation of dielectric loading structures into the waveguide reflector element. An example of this approach is illustrated in FIG. 9(b), which shows a schematic cross-section of a third-order thin-ridge waveguide reflector element 910 embodying the invention. The three waveguides 912a, 912b, 912c have the same height (h=220 nm), the slab thickness is 150 nm, and the substrate thickness is 1.5 µm. The widths of the two outer waveguides are w1=662 nm, and the central waveguide width is w2=578 nm. Pairs of polysilicon dielectric loading strips 914a, 914b, 914c are disposed outboard of each waveguide, within an $SiO_2$ layer 916. The cross-sectional dimensions of the loading strips are hl=160 nm and wl=200 nm. In place of the waveguide height variation employed in the embodiment 900, variations in loading are achieved by selection of the spacing between the waveguides 912a, 912b, 912c and the loading strips 914a, 914b, 914c. In the illustrated embodiment 910 the spacings from the outer waveguides are o1=254 nm, while the spacing from the central waveguide is o2=143 nm. The separation between the loading strips associated with adjacent waveguides is s=1404 nm.

Figure 8A:
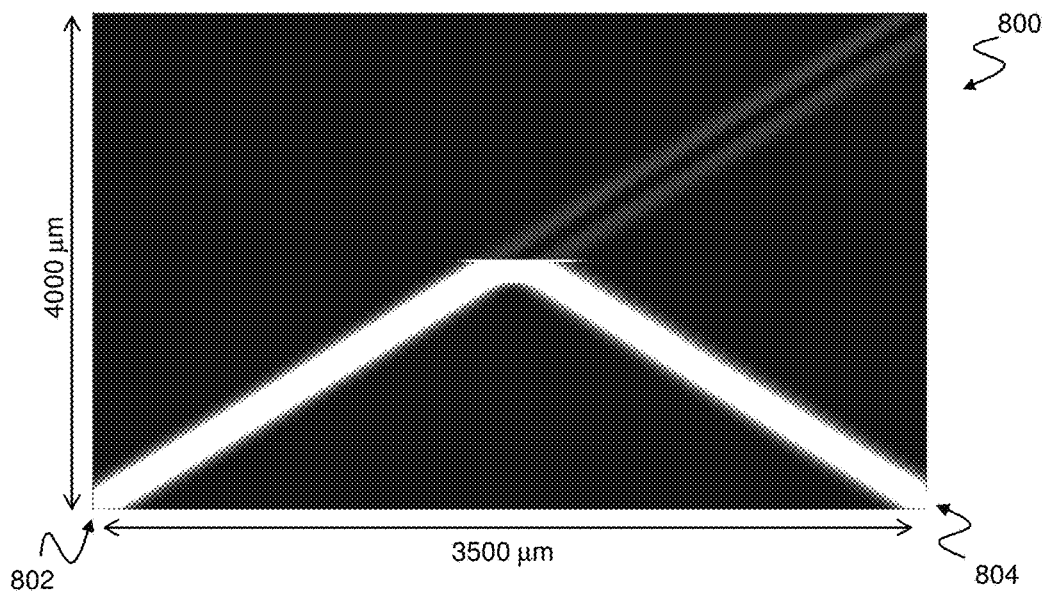
FIGS. 8($a$), ($b$) and ($c$) are examples of computed field intensity for a single waveguide module embodying the invention.
Figure 8B:
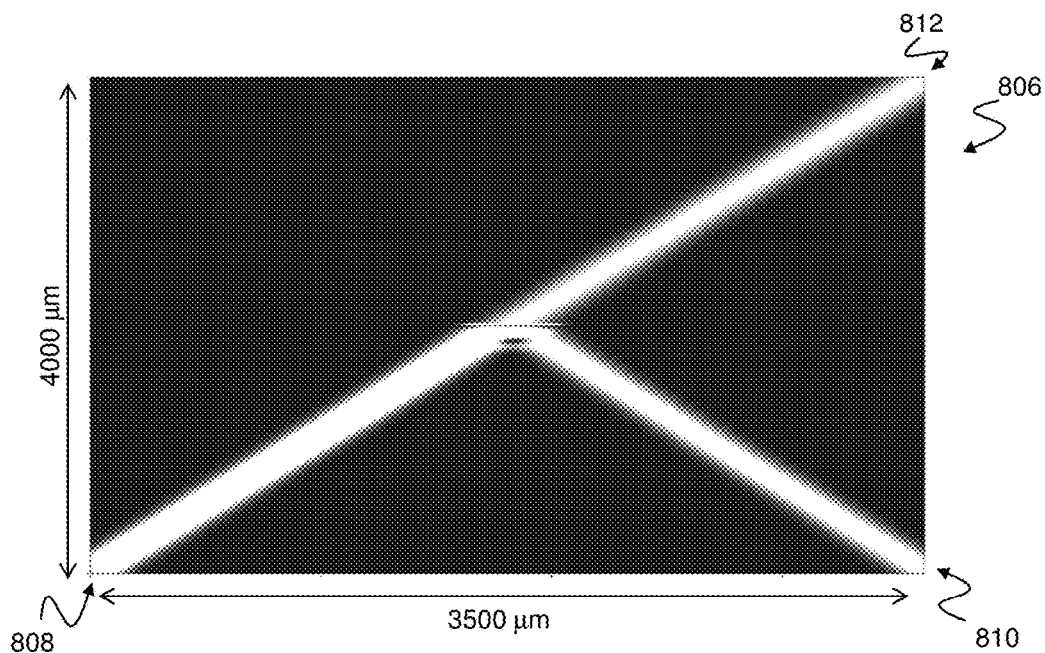
Figure 8C:
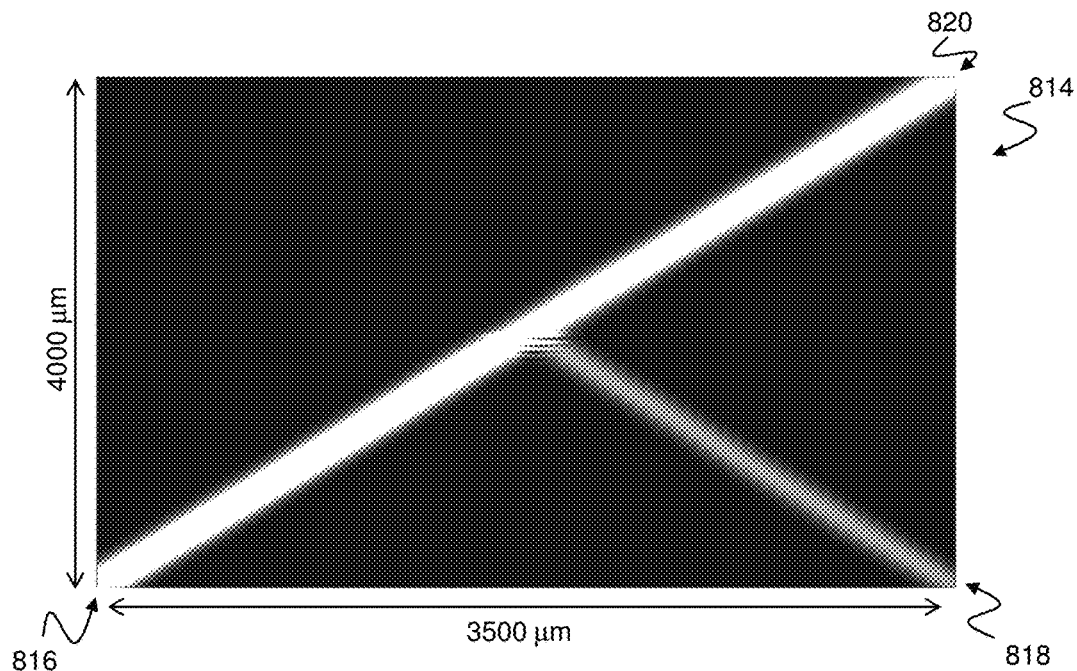
Figure 10A:
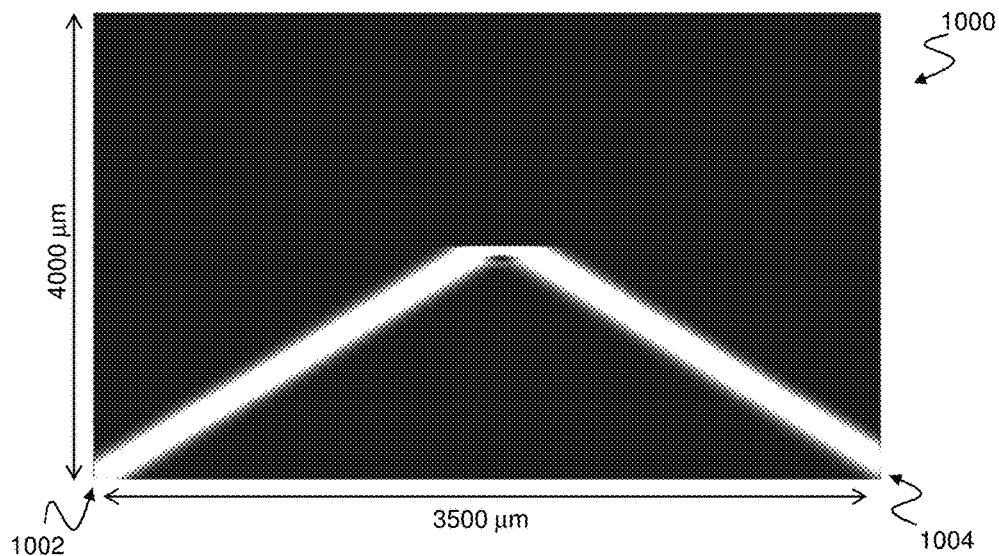
FIGS. 10($a$), ($b$) and ($c$) are examples of computed field intensity for the fifth-order thin-ridge waveguide reflector element which is designed to approximate a Butterworth filter characteristic.
Figure 10B:
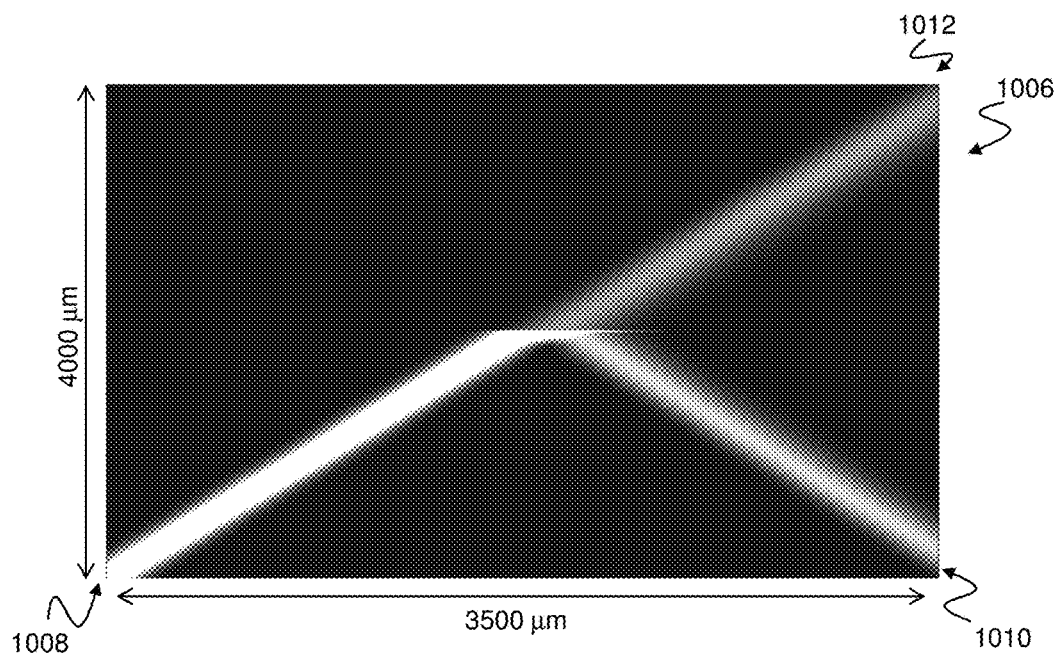
Figure 10C:
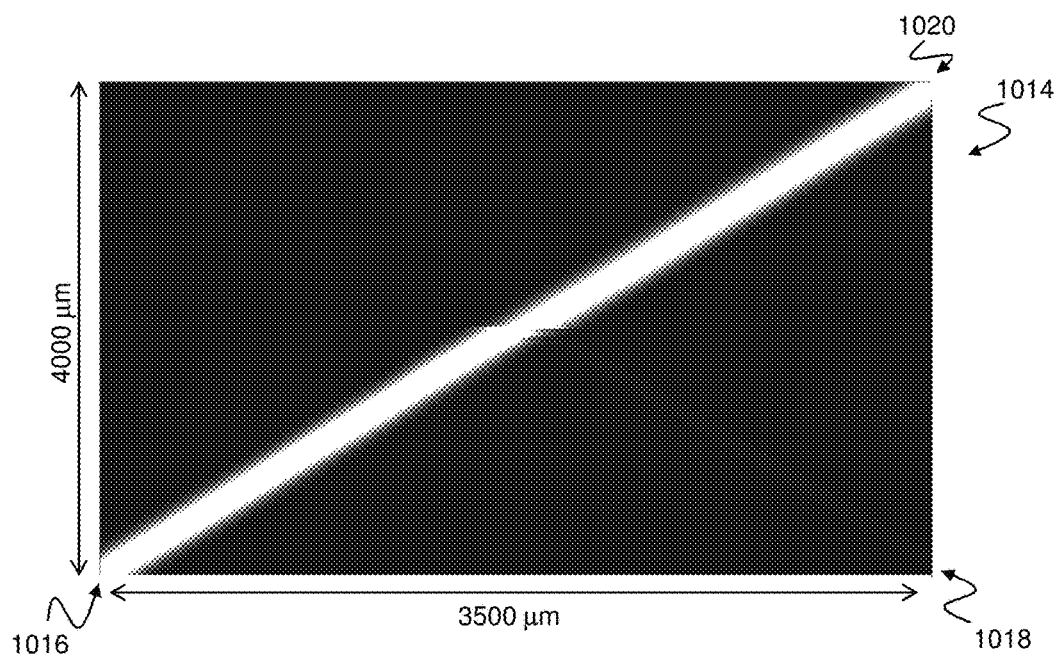

FIGS. 10(a), (b) and (c) show examples of computed field intensity for the fifth-order Butterworth filter 900 corresponding with the scenarios also shown in FIGS. 8(a), (b) and (c). The computed field intensity 1000 shows input beam 1002, having a central wavelength of 1550 nm, reflecting from the waveguide array to produce output beam 1004. The field intensity 1006 shows input beam 1008, having a central wavelength of 1555 nm, being divided into reflected beam 1010 and transmitted beam 1012. The computed field intensity 1014 shows input beam 1016, having a central wavelength of 1560 nm, being substantially transmitted into output beam 1020, with a small residual reflection 1018.

Figure 11A:
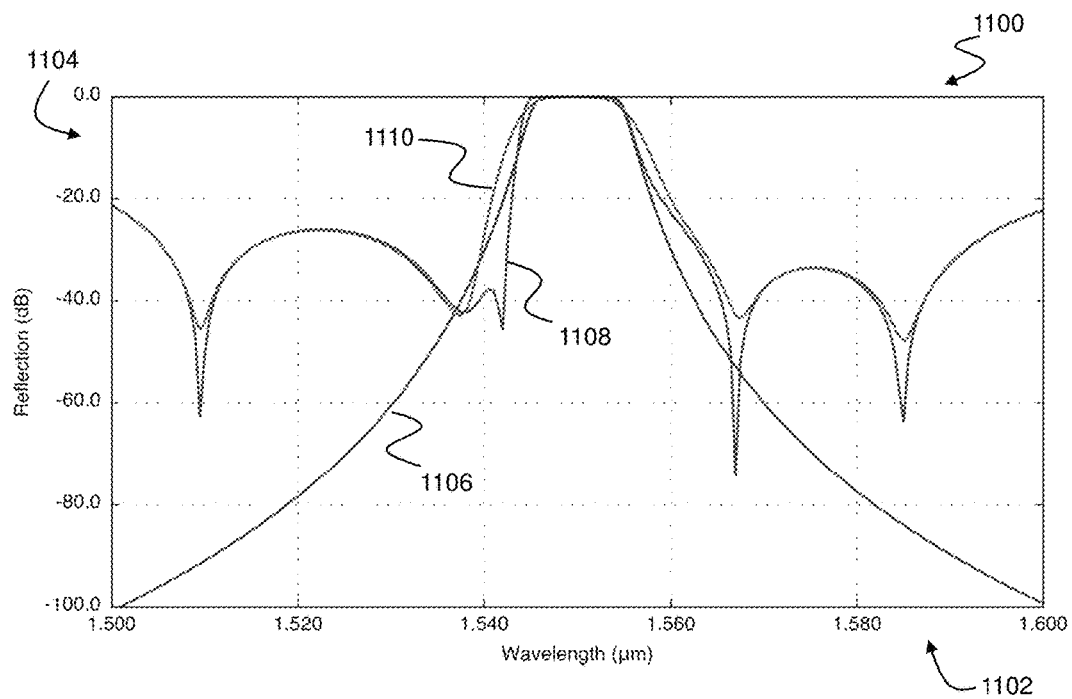
FIG. 11($a$) is a graph showing exemplary reflection spectra corresponding with the reflector represented in FIG. 10.

FIG. 11(a) shows a graph 1100 showing exemplary reflection spectra corresponding with the fifth-order Butterworth filter design 900. The horizontal axis 1102 shows wavelength, while the vertical axis 1104 shows the reflection coefficient, in dB. Three curves are shown, namely the ideal Butterworth filter response 1106, the computed response 1108 for a plane wave input field, and the computed response 1110 for an input field comprising a beam having a Gaussian profile. The results shown in the graph 1100 confirm the effectiveness of the filter synthesis technique for approximating a fifth-order Butterworth filter response. As can be seen, the spectral properties of the structure are influenced by the profile of the beam. Indeed, in alternative embodiments the spectral response may be controlled in a variety of ways, such as by adjusting the resonant strength of the waveguide along it's length, or by adjusting the profile of the beam, e.g. a sinc-profile beam may be employed to approximate a rectangular spectral response). Similarly, structures resulting in a modulation of the waveguide resonance characteristics may also be designed to control the spectral response, e.g. a sinc-function modulation on the waveguide 'Q' may be employed as an alternative means to approximate a rectangular response.

Figure 11B:
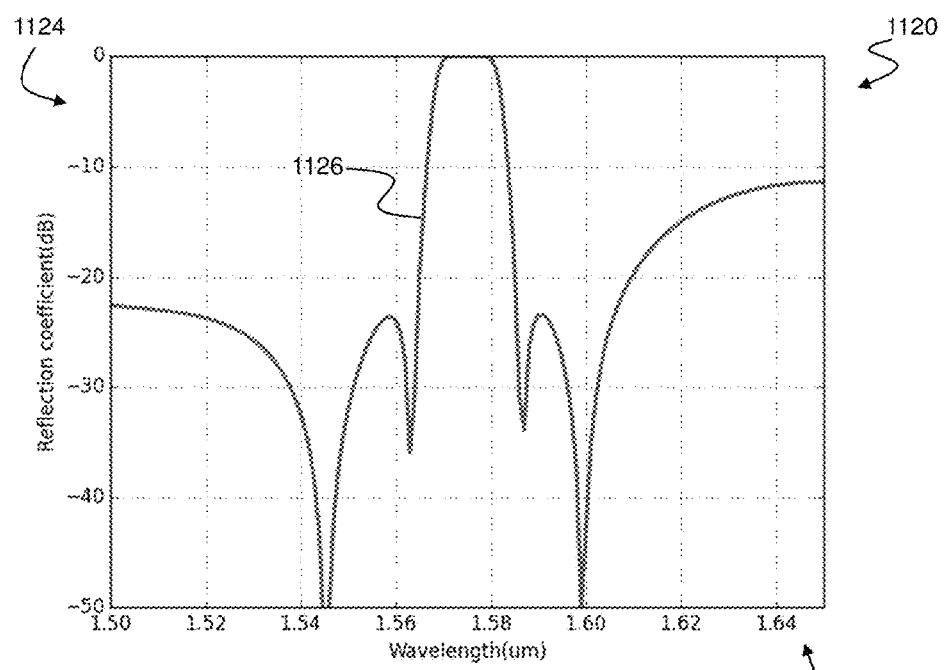

FIG. 11(b) shows a graph 1120 of an exemplary reflection spectrum corresponding with the third-order dielectric-loaded Butterworth filter design 910. The horizontal axis 1122 again shows wavelength, while the vertical axis 1124 shows the reflection coefficient, in dB. The response 1126 is the result of simulation for an input beam angle of 41.79 degrees. This demonstrates the effectiveness of dielectric loading as an alternative to employing different waveguide heights.

Figure 11C:
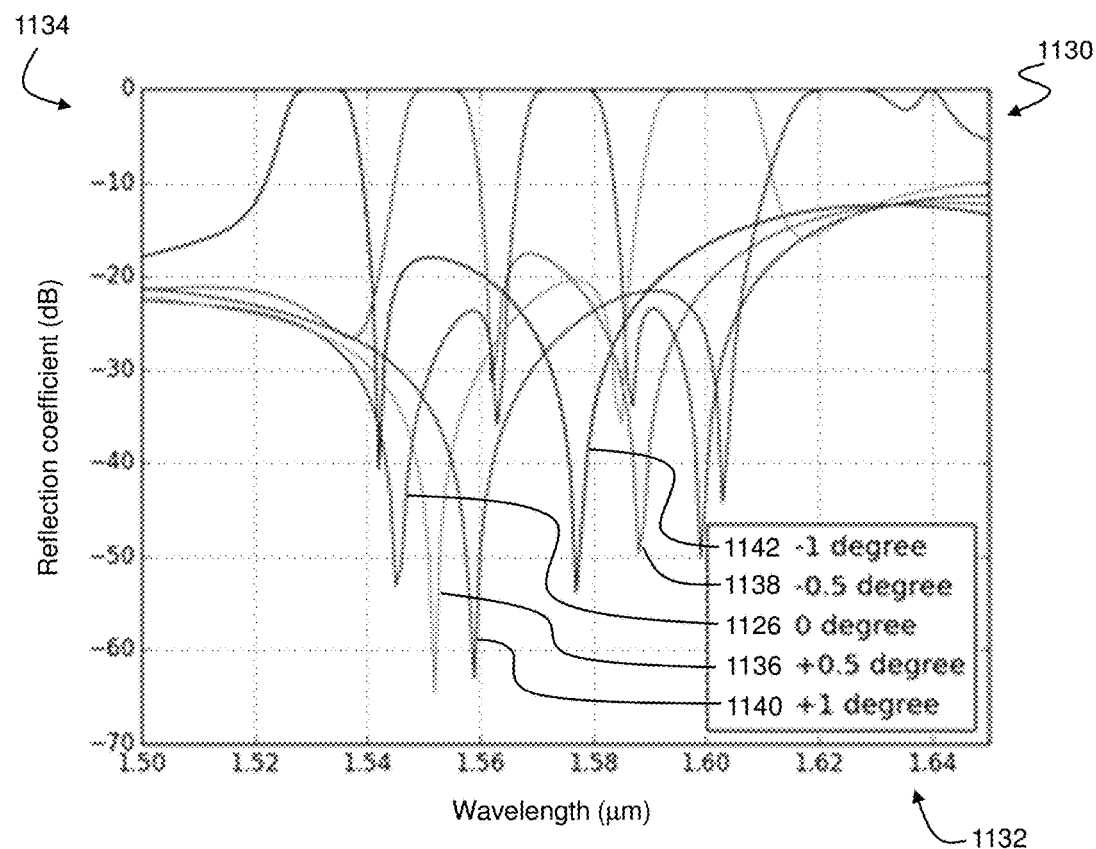

FIG. 11(c) shows a graph 1130 showing a tuning effect of changing the angle of incidence of the light beam to the third-order dielectric-loaded Butterworth filter design 910. The horizontal axis 1132 again shows wavelength, while the vertical axis 1134 shows the reflection coefficient, in dB. For reference, the response 1126 is shown for the design angle of incidence of 41.79 degrees. A slight rotation can be employed as a fine-tuning mechanism. For example, a rotation of +0.5 degrees (to 42.29 degrees) results in the response 1136, in which the pass-band wavelength has been up-shifted by approximately 25 nm. Likewise, a rotation of −0.5 degrees (to 41.29 degrees) results in the response 1138, in which the pass-band wavelength has been down-shifted by approximately 20 nm. Further rotation, e.g. by +1.0 degree or −1.0 degree, results in further wavelength shifts, as shown in the corresponding responses 1140, 1142. Along with the wavelength shift, changes in the pass- and stop-band characteristics are also observed, indicating that for this design 910 a limited angle-tuning range is available, depending upon the required filter parameters and performance.

Similar techniques have been employed to synthesise a fifth-order Chebyshev filter having a 10 nm bandwidth and 0.5 dB stop-band ripple. Referring again to FIG. 9, the parameters for the synthesised filter are: w1=386.5 nm; h1=230 nm; s1=2.341 µm; w2=435.5 nm; h2=227.5 nm; s2=2.390 µm; w3=296 nm; h3=236.5 nm; slab thickness is 200 nm; and substrate thickness is 1.5 µm.

Figure 12A:
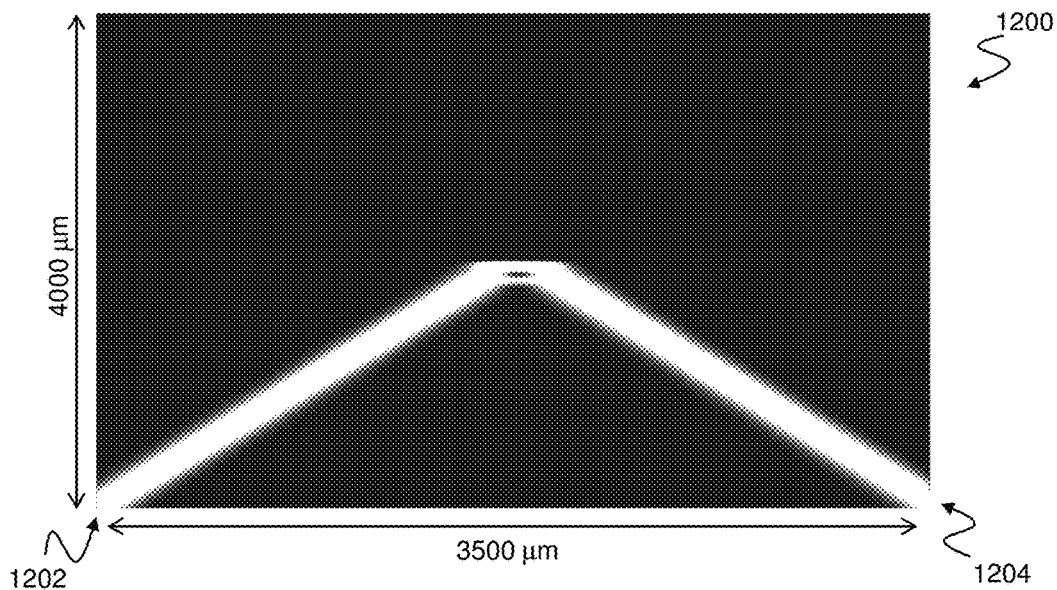
FIGS. 12($a$), ($b$) and ($c$) are examples of computed field intensities for the fifth-order thin-ridge waveguide reflector element which is designed to approximate a Chebyshev filter characteristic.
Figure 12B:
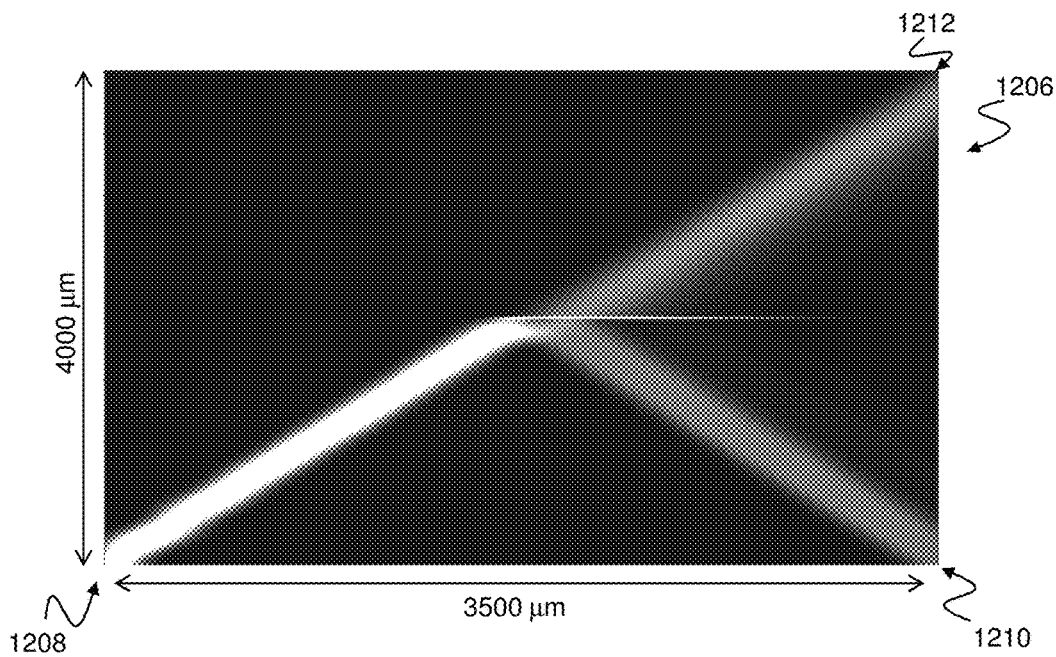
Figure 12C:
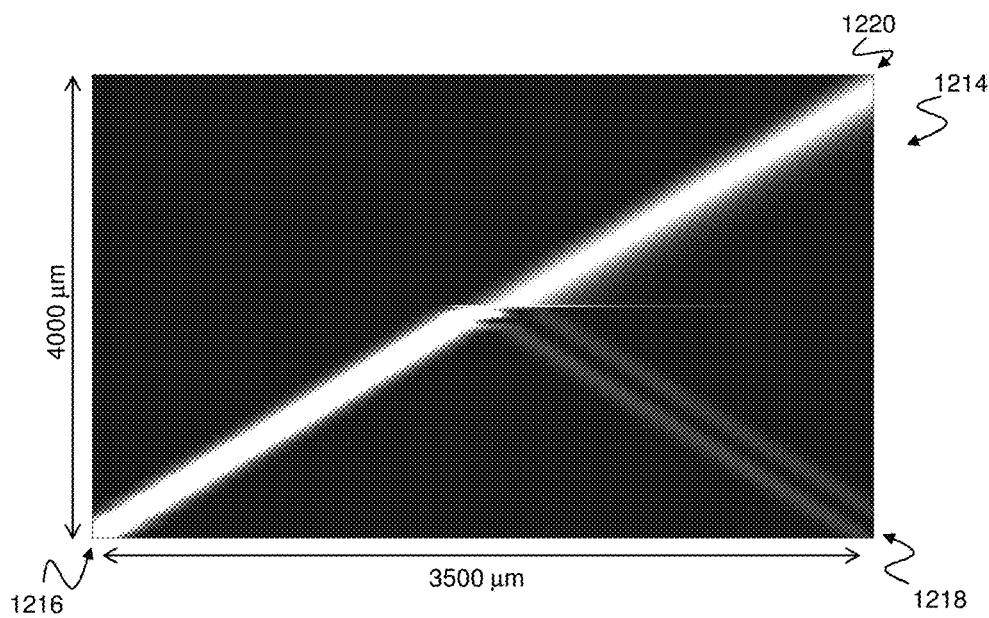

FIGS. 12(a), (b) and (c) show computed field intensities corresponding with the synthesised fifth-order Chebyshev filter. The computed field intensity 1200 shows an input beam 1202 having a central wavelength of 1550 nm being substantially reflected to generate output beam 1204. The field intensity 1206 shows input beam 1208, having a central wavelength of 1555 nm, being partially transmitted 1212 and partially reflected 1210 by the waveguide array. Field intensity 1214 shows an input beam 1216, having a central wavelength of 1560 nm, being substantially transmitted 1220 by the waveguide array, with only a residual reflected beam 1218.

Figure 13:
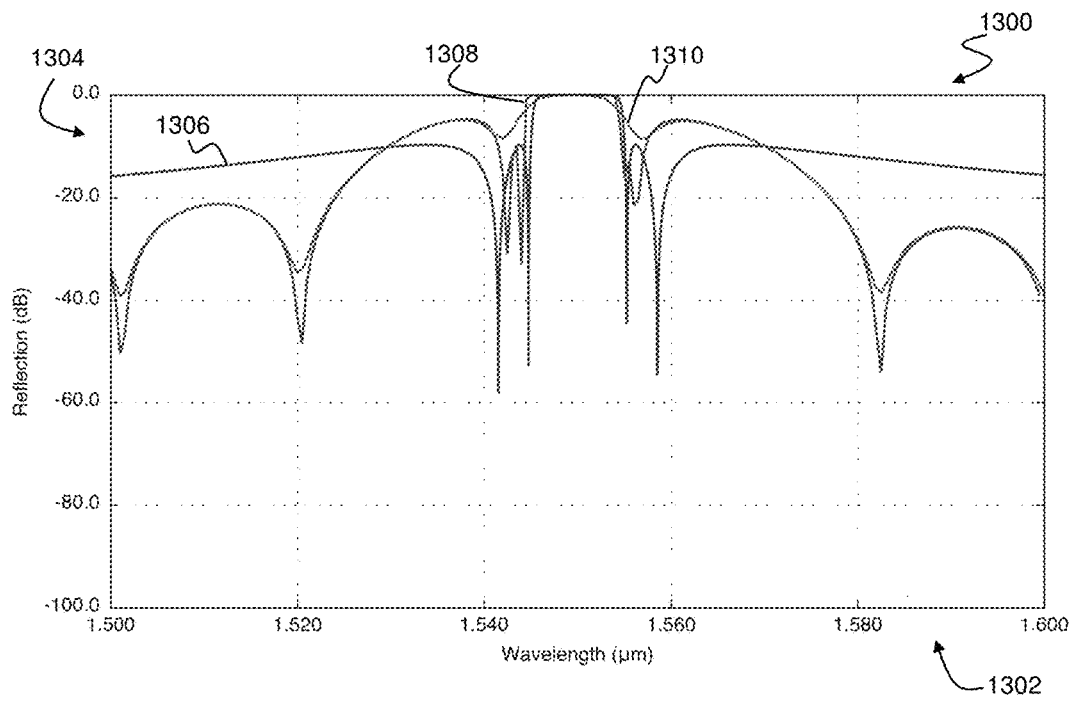
FIG. 13 is a graph showing exemplary reflection spectra corresponding with the reflector represented in FIG. 12.

FIG. 13 is a graph 1300 showing the corresponding reflection spectra for the synthesised fifth-order Chebyshev filter. The horizontal axis 1302 shows wavelength, while the vertical axis 1304 shows reflection coefficient in dB. The graph 1300 includes three curves, being the ideal filter response 1306, the computed response for a plane wave input 1308, and the computed response for an input beam having a Gaussian profile 1310. Again, the results illustrate the effectiveness of the filter synthesis technique for generating waveguide arrays approximating the desired fifth-order Chebyshev filter response.

Modules and waveguide devices embodying the invention have numerous applications in optical signal processing, data communication, sensing, and so forth. A number of these potential applications will now be discussed, by way of example. This is not intended to be an exhaustive list of all possible applications, and other uses of devices and modules embodying the invention may also be apparent to persons skilled in the relevant arts.

A single module embodying the invention may be employed in a wavelength selective optical filter. An input TE beam having a range of wavelengths/frequencies can be selectively filtered by a single waveguide resonator, or by an array of waveguide resonators, as described above. Tuneable filters may be implemented by providing a mechanism to perturb the refractive index of the grating structure. For example, a heating element may be employed to alter the refractive index properties via the thermo-optic effect. Alternatively, a fluid may be applied on top of the grating, having a different refractive index from the silicon layer, in order to tune the spectral response. Electrostatic effects may be used to controllably apply or remove fluids from regions of the grating. As is also known, the refractive index of silicon is dependent upon free carrier concentration, and an electro-optic effect may therefore be achieved by a design enabling the free carrier concentration to be modified in response to an electrical input signal. The waveguides may, for example, be incorporated into a PIN diode structure with the waveguide elements formed within the intrinsic (I) region of the diode. Application of an electrical input signal, i.e. a voltage, to the diode terminals will then result in changes in free carrier concentration within the waveguide region.

In another application, a module having a waveguide resonator embodying the invention may be used as a polarisation filter or splitter. For an input field composed of both TM and TE polarised light, the waveguide structure will strongly reflect the TE beam, and transmit the TM beam, thereby splitting the two polarisation states between first and second outputs of the module. Operated in the reverse direction, the module will act as a polarisation combiner.

Another application of modules embodying the invention is in sensor devices. Such devices may exploit the steep spectral slope that can be achieved between the pass band and stop band of a waveguide array. The wavelength of this transition region is affected by the refractive index of the guided TM mode. This TM mode has a strong evanescent field, and its effective index is therefore strongly dependent upon the outside environment. As a result, the transition wavelength can be strongly affected by small changes in materials located above the waveguides. Where an input optical beam is employed having a wavelength corresponding with the filter transition (e.g. just within the stop band, or just within the pass band) an output signal at the first and/or second outputs of a module will be generated or suppressed in accordance with the effective index of the guided TM mode, which accordingly may be used to sense small changes in the surrounding environment.

Figure 14:
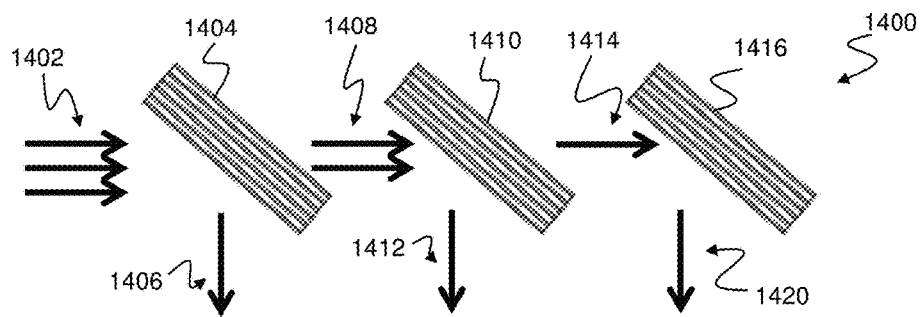
FIG. 14 is a schematic illustration of a wavelength multiplexing/demultiplexing device based upon photonic processing modules embodying the invention.

A further application of modules embodying the invention is as add/drop filters for wavelength division multiplexing (WDM) communications systems. Such a structure 1400 is illustrated schematically in FIG. 14. An input beam comprising multiple wavelength channels 1402 is incident upon a cascade of waveguide array devices embodying the invention. A first array 1404 is designed to reflect a first wavelength 1406, while other wavelengths 1408 are transmitted. Subsequently, a second waveguide array 1410 reflects a second wavelength 1412, while remaining wavelengths 1414 are transmitted. A third array 1416 reflects a third wavelength 1420. The arrangement 1400 also operates in reverse, i.e. can be used for wavelength multiplexing as well as demultiplexing. The cascade of grating structures 1404, 1410, 1416 can be continued in order to multiplex or demultiplex additional wavelengths.

Modules embodying the invention can also be employed as beam splitters. For example, by engineering the design of the waveguide elements a grating coupler may be implemented whereby a percentage of the input TE field is reflected, while the remaining field energy is transmitted through the grating. This is similar to the scenario illustrated in the band edge field intensity calculations shown in FIGS. 8, 10 and 12.

Figure 15:
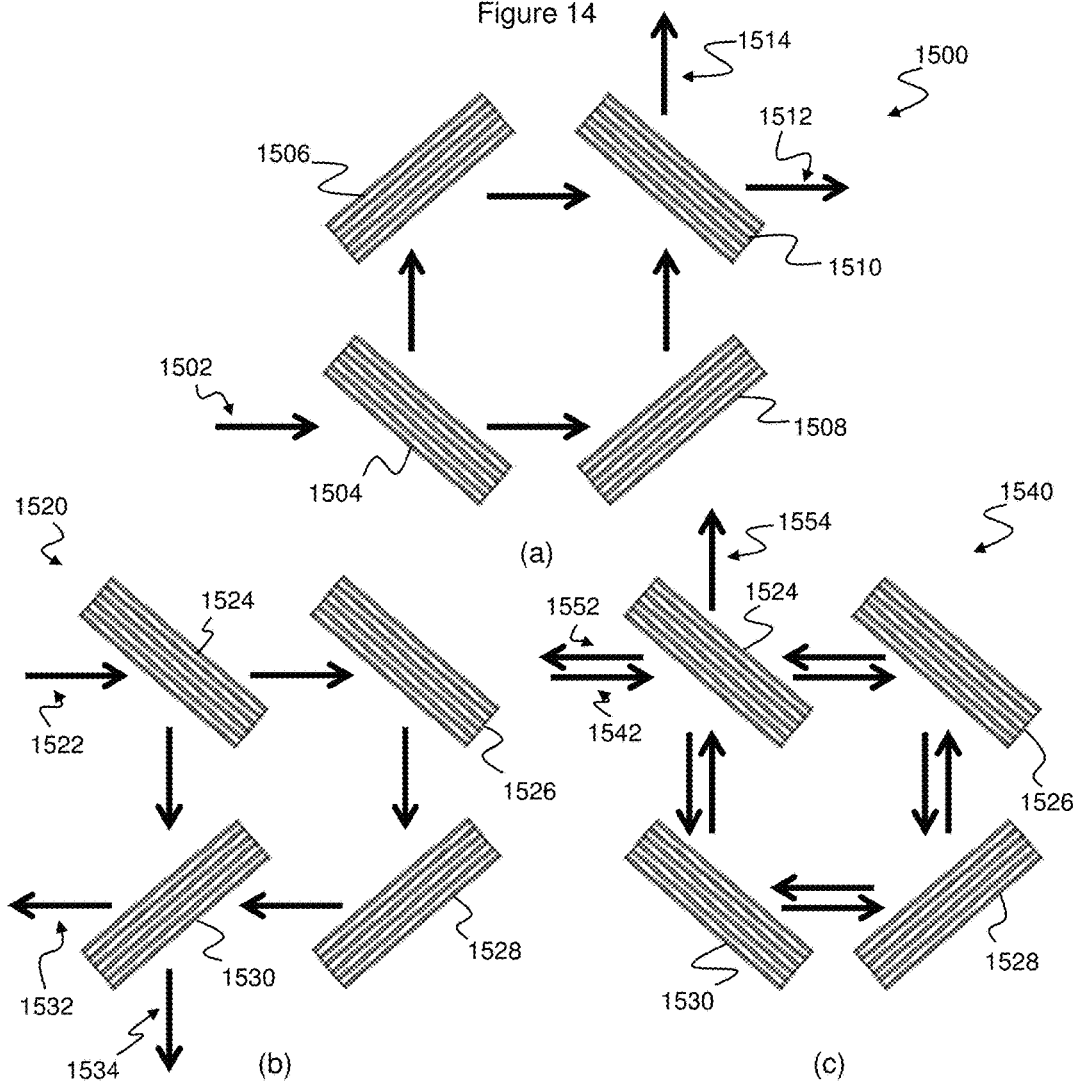
FIGS. 15(a), (b) and (c) are schematic illustrations of interferometer devices based on photonic processing modules embodying the invention.

In view of the ability of modules embodying the invention to implement beam splitters and reflectors, it is also possible to fabricate arrangements implementing various types of interferometer. Three examples are shown in FIGS. 15(a), (b) and (c). For example, a symmetric Mach-Zehnder interferometer 1500 may be designed having an input 1502 which is incident upon a beam splitter 1504 which divides the input beam between two paths, directed to reflectors 1506, 1508. Reflected beams are incident upon a further beam splitter 1510, resulting in two interferometer outputs 1512, 1514.

An asymmetric Mach-Zehnder interferometer 1520 having an input beam 1522 employs corresponding components, in a different arrangement. A first beam splitter 1524 divides the input beam 1522 into two paths, one of which propagates via two reflective arrays 1526, 1528, to a second beam splitter 1530. The second output from the beam splitter 1524 propagates via a shorter path, directly to the second beam splitter 1530. The interferometer 1520 has outputs 1532, 1534.

Finally, FIG. 15(c) illustrates a Sagnac loop interferometer 1540. An input beam 1542 is incident on a beam splitter 1544. Outputs from the beam splitter 1544 propagate in both directions around a loop comprising the three reflectors 1546, 1548, 1550. The counter-propagating beams are recombined at the splitter 1544, producing the two interferometer outputs 1552, 1554.

As will be appreciated, other interferometer structures can also be implemented. Furthermore, such structures may be employed to implement components and devices such as filters, sensors, and switches.

Figure 16:
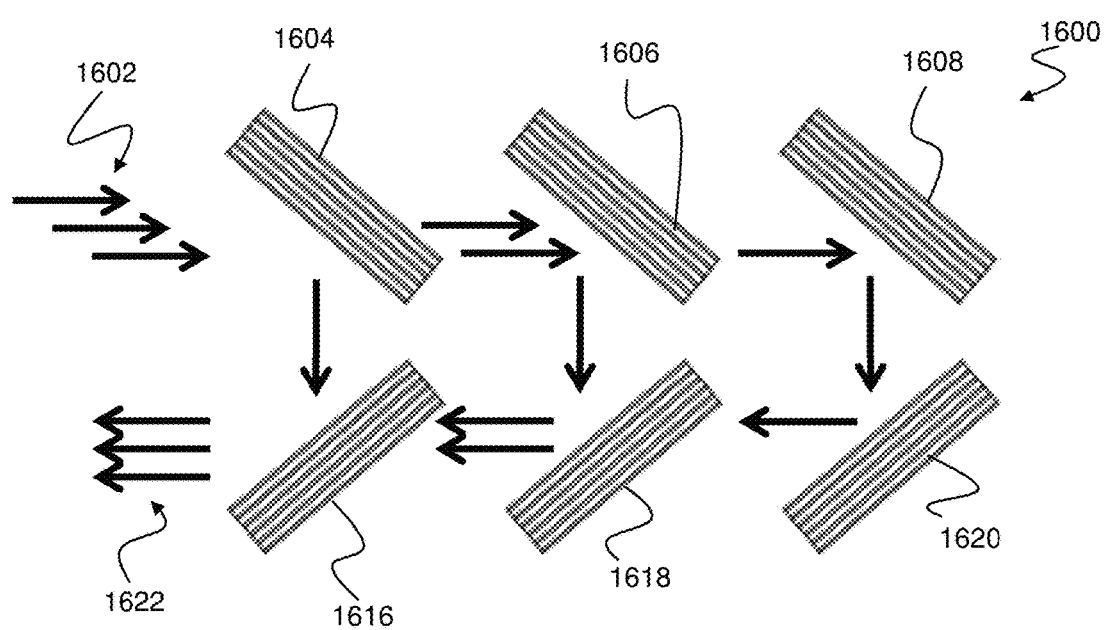
FIG. 16 is a schematic illustration of an exemplary dispersion compensation device based upon photonic processing modules embodying the invention.

FIG. 16 illustrates the application of modules embodying the invention to implement a dispersion compensator 1600. As shown, an input beam 1602 comprises a number of components that have experienced differential delays due to dispersion. A group of three wavelength selective reflectors 1604, 1606, 1608 are arranged in a manner similar to the WDM multiplexer arrangement 1400. Thus each spectral component travels a different distance before being reflected, as shown by the beams 1610, 1612, 1614. A further cascade of reflectors 1616, 1618, 1620 recombine the components into a single output beam 1622. The differential delays between the different wavelength paths result in compensation of the dispersion that is present in the input beam 1602.

Furthermore, structures of the type shown in FIG. 16 may be designed to provide any desired dispersion profile. The dispersion profile may be tuned or reconfigured using the techniques that have already been described for perturbing the refractive index of the waveguide elements.

As has already been noted, the above applications of modules embodying the invention, are not intended to be exhaustive. Other potential applications include the fabrication of one-dimensional and two-dimensional photonic crystal devices. For example, identical waveguides may be arranged in periodic structures, such that a resulting module behaves like a photonic crystal. Defects may be introduced into such an array, e.g. by removing one or more waveguides, thereby creating photonic crystal waveguides for TE polarised light. It may also be possible to form thin-ridge waveguides in a two-dimensional, rather than one-dimensional, array. Such structures could be used to form two-dimensional photonic crystals. These may be capable of performing the functions of a conventional deep-etched photonic crystal, but with easier fabrication and strong interaction with the evanescent TM mode.

Furthermore, in yet another potential application of structures embodying the invention, conversion from TE to TM polarisation may be implemented. For example, by limiting the length of the grating the energy in the input beam may be substantially converted to the TM guided modes within an array of parallel thin-ridge waveguides. The limited length will prevent the TM modes from being converted back into the TE slab mode, and an output TM polarised beam may be generated. Such a structure may also be operated in reverse, in order to convert a TM beam into a TE beam. Grating structures may be implemented having different shapes, such as an elliptical shape, and may be appodised to maximise the conversion between the polarisation states.

While various embodiments, structures, and applications of the invention have been described, these are intended to illustrate the principles and operation of the invention, and are not intended to be an exhaustive discussion of all possible embodiments and/or applications. Accordingly, it will be understood that the scope of the invention is not limited by the disclosed embodiments, but is defined by the following claims.

The invention claimed is:

1. A photonic processing apparatus comprising:
   a high index-contrast waveguide device comprising a substrate, a first layer disposed on the substrate having a first refractive index, and a relatively thin second layer disposed on the first layer which has a second refractive index providing a high index-contrast with the first layer, the device including at least one thin-ridge waveguide element formed in the second layer which supports a guided mode in a longitudinal direction;
   an optical input port configured to direct an input beam into a slab mode of the second layer, the beam being directed to propagate at a predetermined angle θ to the longitudinal direction of the thin-ridge waveguide element, wherein the predetermined angle θ is associated with a resonant coupling between the slab mode of the second layer and the guided mode of the thin-ridge waveguide element, whereby an output beam is generated when the input beam comprises one or more optical components corresponding with the resonant coupling; and
   a first optical output port configured to receive the output beam.

2. The photonic processing apparatus of claim 1, which is a silicon-based photonic processing module wherein:
   the first layer comprises an insulating layer; and
   the second layer comprises a silicon layer (SOI layer).

3. The photonic processing apparatus of claim 1, wherein the guided mode of the thin-ridge waveguide element is a transverse magnetic (TM) mode and the slab mode is a transverse electric (TE) mode.

4. The photonic processing apparatus of claim 1, wherein the output beam is a reflected beam, and the angle of reflection relative to the longitudinal direction of the thin-ridge waveguide element is equal to the predetermined angle θ.

5. The photonic processing apparatus of claim 4, wherein the predetermined angle θ is defined by:

$$\cos\theta = \frac{N_{eff}^{TM}}{N_{slab}^{TE}}$$

wherein $N_{eff}^{TM}$ is the effective index of the guided TM mode, and $N_{slab}^{TE}$ is the effective index of the TE slab mode.

6. The photonic processing apparatus of claim 1, wherein the waveguide device includes a plurality of parallel, coupled, thin-ridge waveguide elements.

7. The photonic processing apparatus of claim 6, wherein a number, and associated dimensions, of the parallel, coupled, thin-ridge waveguide elements are selected to achieve a desired characteristic spectral response of the high index-contrast waveguide device.

8. The photonic processing apparatus of claim 6, wherein the waveguide device further comprises a plurality of dielectric loading elements disposed adjacent to, and spaced apart from, the waveguide elements, and wherein a number, and associated dimensions, of the parallel, coupled, thin-ridge waveguide elements, and a number, associated dimensions, and spacings of the dielectric loading elements from the waveguide elements, are selected to achieve a desired characteristic spectral response of the high index-contrast waveguide device.

9. The photonic processing apparatus of claim 7, wherein the characteristic spectral response approximates a Butterworth filter, a Chebyshev filter, or an elliptic filter.

10. The photonic processing apparatus of claim 8, wherein the characteristic spectral response approximates a Butterworth filter, a Chebyshev filter, or an elliptic filter.

11. The photonic processing apparatus of claim 4, which further comprises a second optical output port configured to receive a transmitted beam which comprises one or more components not corresponding with the resonant coupling.

12. The photonic processing apparatus of claim 1, wherein the high index-contrast waveguide device further comprises refractive index modulating means adapted to enable a refractive index of at least a portion of the second layer to be perturbed.

13. The photonic processing apparatus of claim 12, wherein the refractive index modulating means is a heating element.

14. The photonic processing apparatus of claim 12, wherein the refractive index modulating means is a fluid.

15. The photonic processing apparatus of claim 12, wherein the second layer comprises a semiconductor material, and the refractive index modulating means is an electro-optic modulator configured to modify a free carrier concentration in the thin-ridge waveguide element in response to an electrical input signal.

16. The photonic processing apparatus of claim 15, wherein the electro-optic modulator comprises a PIN diode, wherein the thin-ridge waveguide element is formed within the intrinsic (I) region of the diode.

17. The photonic processing apparatus of claim 1 wherein the angle at which the optical input port is configured to direct the input beam is adaptable over a range, whereby a characteristic wavelength of the resonant coupling is tunable.

18. A wavelength-selective optical filter comprising the photonic processing apparatus according to claim 1.

19. A wavelength-selective multiplexer/demultiplexer comprising one or more photonic processing apparatuses according to claim 11.

20. A tunable optical filter comprising t photonic processing apparatus according to claim 12.

21. A polarisation beam splitter comprising the photonic processing apparatus according to claim 1.

22. A sensor comprising the photonic processing apparatus according to claim 1.

23. A beam splitter comprising t photonic processing apparatus according to claim 11.

24. An interferometer comprising the plurality of processing apparatus according to claim 1.

25. A dispersion engineering device comprising h plurality of photonic processing apparatus according to claim 1.

26. A method comprising:
   directing an input beam into a slab mode of a photonic processing structure at a predetermined angle θ to a longitudinal direction of a thin-ridge waveguide element in the photonic processing structure, wherein the predetermined angle θ is associated with a resonant coupling between the slab mode and a guided mode of the thin-ridge waveguide element, wherein the photonic processing structure includes a substrate, a first layer disposed on the substrate having a first refractive index, and a relatively thin second layer that supports the slab mode disposed on the first layer with a second refractive index providing a high index contrast with the first layer; and generating an output beam when the input beam comprises one or more optical components corresponding with the resonant coupling.

* * * * *